(12) United States Patent
Nishihara et al.

(10) Patent No.: US 7,993,887 B2
(45) Date of Patent: Aug. 9, 2011

(54) MICROORGANISM, LIPID-MODIFYING AGENT, AND THE METHOD OF MANUFACTURING 2-ACYL LYSOPHOSPHOLIPIDS

(75) Inventors: Masaaki Nishihara, Tokyo (JP); Masazumi Kamata, Tokyo (JP); Kohji Yamaguchi, Yokohama (JP); Kazunaga Yazawa, Fujisawa (JP)

(73) Assignee: Tokyo University of Marine Science and Technology, Tokyo (JP)

( * ) Notice: Subject to any disclaimer, the term of this patent is extended or adjusted under 35 U.S.C. 154(b) by 798 days.

(21) Appl. No.: 11/920,856

(22) PCT Filed: Apr. 11, 2006

(86) PCT No.: PCT/JP2006/307605
§ 371 (c)(1),
(2), (4) Date: Nov. 21, 2007

(87) PCT Pub. No.: WO2006/126334
PCT Pub. Date: Nov. 30, 2006

(65) Prior Publication Data
US 2009/0029428 A1 Jan. 29, 2009

(30) Foreign Application Priority Data
May 26, 2005 (JP) ................................ 2005-154253

(51) Int. Cl.
*C12N 1/20* (2006.01)
*C12P 7/64* (2006.01)
*C12N 9/20* (2006.01)
(52) U.S. Cl. ...................... 435/134; 435/253.3; 435/198
(58) Field of Classification Search ........................ None
See application file for complete search history.

(56) References Cited

OTHER PUBLICATIONS

N. Tsukagohi et al. "structure ans Synthesis of a Lipid-containing Bacteriophage", Eur. J. Biochem. 60: 603-613 (1975).*
R.T. Espejo et al. "properties and Characterization of the Host Bacterium of Bacteriophage PM2", J. Bacteriol. 95(5):1887-1891. (May 1968).*
Nishihara, Masaaki, et al., "Isolation of phospholipase $A_1$ producing. strain originating from marine organisms," Japan Society for Bioscience, Biotechnology, and Agrochemistry, Annual conference presentations database (2005), Mar. 5, 2005, p. 205, (Abstract 30D087a).
Kamata, Masazumi, et al., "Phospholipase $A_1$ produced by marine bacteria," The 37th Oil Chemistry Symposium, Presentation overview, Sep. 16, 1998, p. 94 (Abstract 1E17).
Yazawa, Kazunaga, et al., "Phospholipase $A_1$ produced by DHA producing isolate and its use," *Journal of Lipid Nutrition*, Japan Society for Lipid Nutrition, Presentation overview, Aug. 24, 1998, p. 103, vol. 7, No. 2, (Abstract 001).
Nishihara, Masaaki, et al., "Characteristics of $PLA_1$ producing *Pseudomonas* sp. HFKI0020 derived from marine organisms," 8th Conference of Japan Society for Marine Biotechnology, May 28, 2005, p. 86, (Abstract 1-13).
ishihara, Masaaki, et al., "The hydrolytic property of phospholipase $A_1$ in a culture supernatant of *Pseudomonas* sp. HFKI0020 strain," Japanese Society of Enzyme Engineering, Presentation overview, Oct. 25, 2005, p. 59, (Abstract B-5).

* cited by examiner

*Primary Examiner* — Rebecca Prouty
(74) *Attorney, Agent, or Firm* — Oliff & Berridge, PLC

(57) ABSTRACT

The present invention provides a new supply source of phospholipase $A_1$, which is useful for phospholipid modification and lipid biochemical research, and offers a method capable of efficiently manufacturing a large amount of high DHA content phospholipids and lysophospholipids. A novel microorganism HFKI-0020 (FERM AP-20545) of the genus *Pseudomonas* which produces enzymes with phospholipase $A_1$ activity can be used as a new supply source of enzymes with the phospholipase $A_1$ activity. A lipid-modifying agent containing an effective dose of enzymes with the phospholipase $A_1$ activity produced by those novel microorganisms allows the efficient mass-production of lysophospholipids.

10 Claims, 1 Drawing Sheet

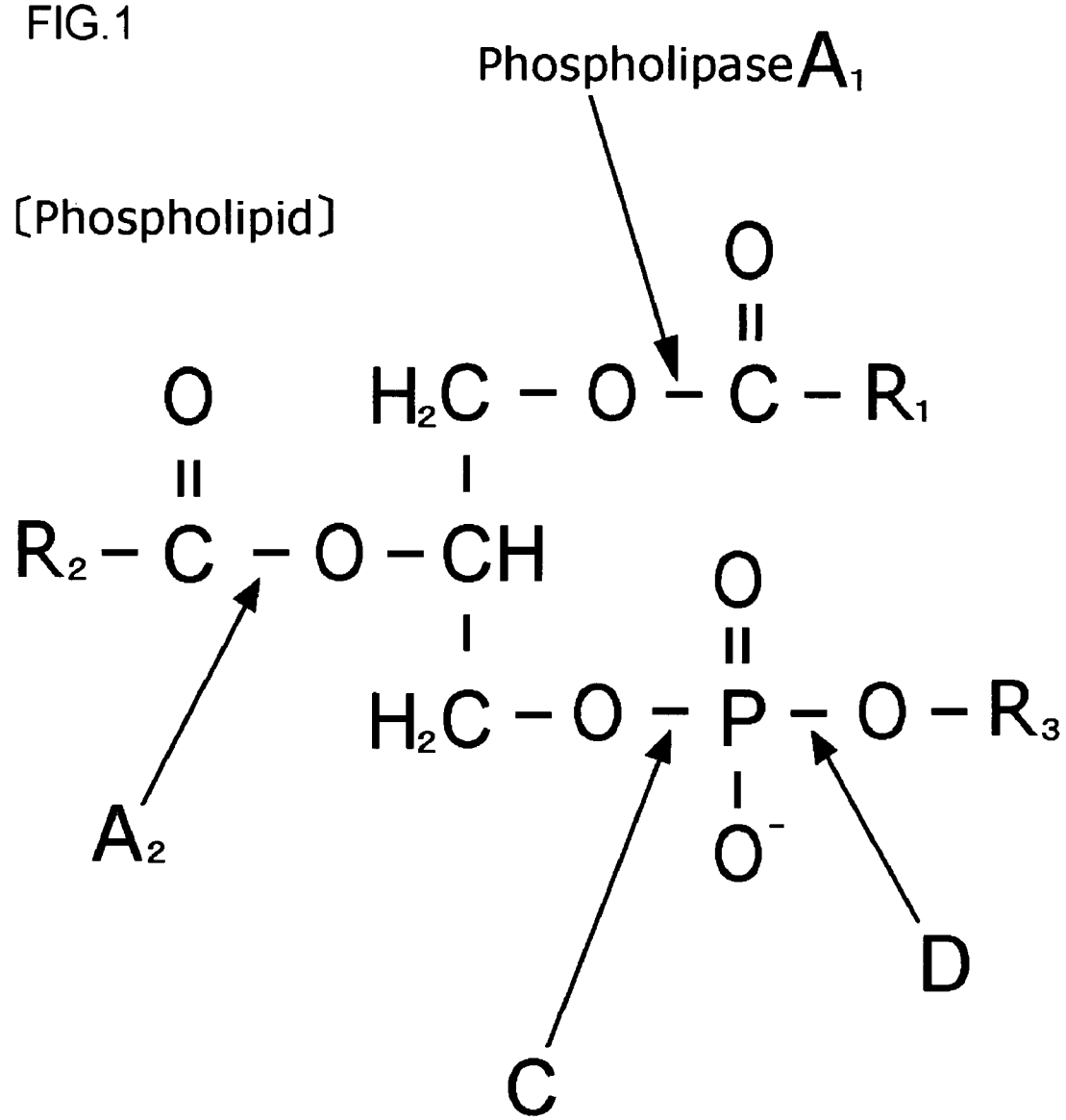

SEQUENCE LISTING

<160> NUMBER OF SEQ ID NOS: 1

<210> SEQ ID NO 1
<211> LENGTH: 1497
<212> TYPE: DNA
<213> ORGANISM: Pseudomonas sp. HFKI-0020

<400> SEQUENCE: 1

```
gagtttgatc ctggctcaga ttgaacgctg gcggcaggcc taacacatgc aagtcgagcg      60
gatgacagga gcttgctcct gaattcagcg gcggacgggt gagtaatgcc taggaatctg     120
cctggtagtg ggggacaacg tttcgaaagg aacgctaata ccgcatacgt cctacgggag     180
aaagcagggg accttcgggc cttgcgctat cagatgagcc taggtcggat tagctagttg     240
gtgaggtaat ggctcaccaa ggcgacgatc cgtaactggt ctgagaggat gatcagtcac     300
actggaactg agacacggtc cagactccta cgggaggcag cagtggggaa tattggacaa     360
tgggcgaaag cctgatccag ccatgccgcg tgtgtgaaga aggtcttcgg attgtaaagc     420
actttaagtt gggaggaagg gcattaacct aatacgttag tgttttgacg ttaccgacag     480
aataagcacc ggctaactct gtgccagcag ccgcggtaat acagagggtg caagcgttaa     540
tcggaattac tgggcgtaaa gcgcgcgtag gtggtttgtt aagttggatg tgaaatcccc     600
gggctcaacc tgggaactgc attcaaaact gacaagctag agtatggtag agggtggtgg     660
aatttcctgt gtagcggtga aatgcgtaga tataggaagg aacaccagtg gcgaaggcga     720
ccacctggac tgatactgac actgaggtgc gaaagcgtgg ggagcaaaca ggattagata     780
ccctggtagt ccacgccgta aacgatgtca actagccgtt gggagccttg agctcttagt     840
ggcgcagcta acgcattaag ttgaccgcct ggggagtacg gccgcaaggt taaaactcaa     900
atgaattgac gggggcccgc acaagcggtg gagcatgtgg tttaattcga agcaacgcga     960
agaaccttac caggccttga catccaatga actttccaga gatggattgg tgccttcggg    1020
aacattgaga caggtgctgc atggctgtcg tcagctcgtg tcgtgagatg ttgggttaag    1080
tcccgtaacg agcgcaaccc ttgtccttag ttaccagcac gtaatggtgg gcactctaag    1140
gagactgccg gtgacaaacc ggaggaaggt ggggatgacg tcaagtcatc atggccctta    1200
cggcctgggc tacacacgtg ctacaatggt cggtacaaag ggttgccaag ccgcgaggtg    1260
gagctaatcc cataaaaccg atcgtagtcc ggatcgcagt ctgcaactcg actgcgtgaa    1320
gtcggaatcg ctagtaatcg tgaatcagaa tgtcacggtg aatacgttcc cgggccttgt    1380
acacaccgcc cgtcacacca tgggagtggg ttgcaccaga agtagctagt ctaaccttcg    1440
ggaggacggt taccacggtg tgattcatga ctggggtgaa gtcgtaacaa ggtagcc       1497
```

MICROORGANISM, LIPID-MODIFYING AGENT, AND THE METHOD OF MANUFACTURING 2-ACYL LYSOPHOSPHOLIPIDS

TECHNICAL FIELD OF THE INVENTION

The present invention is related to a novel microorganism in the genus *Pseudomonas* that produces enzymes with phospholipase $A_1$ activity, and a lipid-modifying agent containing an effective dose of enzymes with the phospholipase $A_1$ activity produced by those novel microorganisms. It further relates to the method of manufacturing 2-acyl lysophospholipids using the enzymes with the phospholipase $A_1$ activity produced by those novel microorganisms for hydrolyzing phospholipids in order to obtain the 2-acyl lysophospholipids.

BACKGROUND ART

Since lysophospholipids have a higher surface-activity when compared to general phospholipids, it offers an improvement in emulsion stability, texture, and elasticity of food to that provided by phospholipids, while allowing a reduction in the amount of other emulsifiers. Thus, the lysophospholipids are known as a highly effective lipid formation when applied to foods. Other than food applications, it also has value as an emulsifier for cosmetics.

At present, the industrial preparative method of lysophospholipids is known to employ phospholipase $A_2$. However, the problems are that this phospholipase $A_2$ is an enzyme derived mainly from a porcine pancreas, and the emulsion by 1-acyl lysophospholipids is significantly low in the isolation rate of the oil layer compared to the emulsion by 2-acyl lysophospholipids (Lecture number P10, the 35th oil chemistry symposium).

Since phospholipases do not hydrolyze triglycerides, it will not produce diglycerides and monoglycerides even in the presence of triglycerides in the substrate, not interfering with the generation of lysophospholipids, which are the hydrolyzed products of phospholipids.

As disclosed in Japanese Patent Application Laid Open No. 6-62850, Japanese Patent Application Laid Open No. 7-31472, and Japanese Patent Application Laid Open No. 7-222592, the preparation methods for phospholipase $A_1$ derived from fungus, such as filamentous fungus, have been developed. However, those require a long period of time for cultivation, and the operation to extract enzymes from a culture medium with bacterial bodies is cumbersome.

Phospholipase $A_1$ exists in animal pancreases and livers, and microorganisms contribute to the metabolic turnover of lipids in cooperation with phospholipase $A_2$. It is also a useful enzyme for analyzing the internal distribution of fatty acid molecules of phospholipids and for lipid biochemical research.

Patent document 1: Japanese Patent Application Laid Open No. 6-62850
Patent document 2: Japanese Patent Application Laid Open No. 7-31472
Patent document 3: Japanese Patent Application Laid Open No. 7-222592

DISCLOSURE OF INVENTION

Problem Solved by the Invention

The purpose of the present invention is to provide a new supply source of phospholipase $A_1$, which is useful in phospholipid modification and lipid biochemical research, and also to offer a method capable of efficiently preparing a large amount of high DHA content phospholipids and lysophospholipids.

Means of Solving the Problem

In order to solve the above-described problems, the inventors, as a result of an earnest study, detected the phospholipase $A_1$ activity among a culture solution of microorganisms (HFKI-0020), which belong to the genus *Pseudomonas*.

Therefore, the present invention provides microorganisms (HFKI-0020), which belong to the genus *Pseudomonas* and secrete enzymes with the phospholipase $A_1$ activity, a lipid-modifying agent with an active ingredient of a culture solution containing the enzymes, and also a method of manufacturing 2-acyl lysophospholipids by using this lipid-modifying agent for hydrolyzing phospholipids.

Advantageous Effect of the Invention

According to the present invention, it has an advantageous effect of providing a new supply source of enzymes with the phospholipase $A_1$ activity, which is useful in phospholipid modification and lipid biochemical research.

In addition, according to the microorganisms of the present invention, since the enzymes with phospholipase $A_1$ activity are secreted into the culture solution outside the bacterial body, it has an advantageous effect of producing a large amount of enzymes compared to bacteria that accumulate enzymes inside the bacterial body.

In addition, according to the microorganisms of the present invention, since enzymes with the phospholipase $A_1$ activity are secreted into the culture solution outside the bacterial body, it has an advantageous effect of making fractionation easy, allowing an easy collection of the enzymes from the culture solution compared to collecting enzymes from bacteria that produce the enzymes inside the bacterial body.

In addition, according to the lipid-modifying agent (culture solution) of the present invention, it has an advantageous effect of efficiently producing 2-acyl lysophospholipids in a cool condition at a temperature as low as 10 degrees Celsius. Furthermore, if DHA (docosahexaenoic acid) is used as the 2-acyl group, high DHA content phospholipids and lysophospholipids can be produced.

BRIEF DESCRIPTION OF THE DRAWINGS

FIG. 1 is an illustration indicating the state of hydrolysis by the phospholipid phospholipase.

BEST MODE FOR CARRYING OUT THE INVENTION

In the present invention, the culture solution includes all of the culture productions obtained from the cultivation of *Pseudomonas* sp. HFKI-0020 whether or not the culture contains the bacterial body. The culture solution of the present invention can be obtained through commonly used isolation and purification methods after the cultivation of these strains in accordance with the usual method, for example, in a culture medium containing peptone and yeast extract. The recommended preparation method and manufacturing method of the present invention are to use a culture medium (culture supernatant) from which the bacterial bodies are removed by centrifugation. As a substrate, any phospholipids with an ester bond at the sn-1 position can be used, for example, naturally existing phospholipids derived from such plants as soybeans and rapeseeds, land and marine animals like salmon roe, squid, and egg yolk, and microorganisms such as bacteria and yeast, and chemically and enzymatically prepared phospholipids.

As a result of the identification of the microorganism (HFKI-0020), it was identified as the genus *Pseudomonas*. The methods of morphological observation, physiological and biochemical property tests, and 16S rDNA (16S rRNA gene) base sequence analysis, as well as the results of the microbial tests and the analysis are presented as follows.

The culture method of the microorganisms (HFKI-0020), which belong to the genus *Pseudomonas*, uses a K28 culture medium. Table 1 shows the composition of the K28 culture medium. The cultivation was performed under aerobic conditions at a cultivation temperature of 10 degrees Celsius for five days.

TABLE 1

Composition of K28 culture medium

| Medium component | Additive amount |
|---|---|
| Peptone (Becton Dickinson, MD, U.S.A.) | 5.0 g |
| Yeast extract (Becton Dickinson, MD, U.S.A.) | 1.0 g |
| Agar (Becton Dickinson, MD, U.S.A.) | 15.0 g |
| ½ concentration of artificial seawater | 1.0 L |

As a bacterial property test, a light microscope BX50F4 (Olympus, Japan) was used to observe cell morphology, Gram stainability, presence of spores, and presence of mobility with the flagellum. In addition, colony morphology was observed on the plane table of the K28 culture medium. Furthermore, the catalase reaction, oxidase reaction, production of acid and gas from glucose, and oxidation and fermentation (O/F) of glucose were also tested. Results of the bacterial property test are shown in Table 2.

TABLE 2

Results of bacterial property test

| Test items | Results | |
|---|---|---|
| Cell shape | Rod (0.8 to 1.0 × 2.0 to 3.0 micrometers) | |
| Gram stainability | − | |
| Presence of spores | − | |
| Mobility | + | |
| Colony shape | Culture time | 48 hours |
| | Diameter | 2.0 to 3.0 mm |
| | Color tone | Lemon yellow |
| | Shape | Circular |
| | Topography | Lens-shaped |
| | Fringe | Whole border |
| | Surface shape | Smooth |
| | Transparency | Opaque |
| | Viscosity | Butter-like |
| Growth temperature test | 37 | + |
| (degrees Celsius) | 45 | +w |
| Catalase reaction | + | |
| Oxidase reaction | + | |
| Production of acid and gas from glucose | −/− | |
| (acid production/gas production) | | |
| O/F test (Oxidation/Fermentation) | −/− | |

+: Positive,
−: Negative,
+w Weak reaction

Results of the physiological and biochemical property tests are shown in Table 3.

TABLE 3

Results of physiological and biochemical property tests

| Substrate, reaction and enzyme activity | Results | Substrate, reaction and enzyme activity | Results |
|---|---|---|---|
| Nitrate reduction* | − | D-Mannitol** | + |
| Indole production* | − | N-acetyl-D-glucosamine** | + |
| Glucose acidification* | − | Maltose** | − |
| Arginine dihydrolase* | + | Potassium gluconate** | + |
| Urease* | − | n-Capric acid** | + |
| Esculin hydrolysis* | − | Adipic acid** | − |
| Gelatin hydrolysis* | + | DL-Malic acid** | + |
| Beta galactosidase* | − | Sodium citrate** | + |
| Glucose** | + | Phenyl acetate** | − |
| L-Arabinose* | + | Cytochrome oxidase* | + |
| D-Mannose** | + | | |

*Biochemical test,
**Assimilation test

As an additional test, a fluorochrome production test was performed on King's B agar medium. The results of the test are shown in Table 4.

TABLE 4

Result of additional test

| Test item | Result |
|---|---|
| Fluorochrome production on King's B agar medium | + |

For the 16S rDNA base sequence analysis, InstaGene Matrix (BIO RAD, CA, U.S.A.) was used to extract the genome DNA in accordance with the procedural protocol of the BIO-RAD Laboratories. The extracted genome DNA was used as a mold to amplify the range between 1500 to 1600 bp, the whole base sequence of the 16S ribosomal RNA genome (16S rDNA) by PCR. Then, the amplified 16S rDNA was sequenced to obtain a sample 16S rDNA base sequence. Ready-To-Go PCR Beads (Amersham Pharmacia Biotech, NJ, USA), primer 9F, and primer 1510R were used for the PCR. ABI Prism BigDye Terminator v3.1 Kit (Applied Biosystems, CA, USA), and eight different sequence primers were used for the cycle sequencing. GeneAmp PCR System 9600 (Applied Biosystems, CA, USA), and ABI PRISM 3100 DNA Sequencer (Applied Biosystems, CA, USA) were used, respectively, as a thermal cycler and a DNA Sequencer. Then, AutoAssembler 2.1 (Applied Biosystems, CA, USA) was used to connect fragments of the obtained base sequence. The basic operations from the PCR through to the cycle sequencing were performed in accordance with the protocol of each kit.

The 16S rDNA base sequence of the microorganisms (HFKI-0020), which belong to the genus *Pseudomonas* is shown in the sequence number 1 of the sequence table.

The above-listed base sequence was searched for homology in two different base sequence databases.

First, as analysis software, MicroSeq Microbial Identification System Software V.1.4.1 (Applied Biosystems, CA, USA) was used to analyze the base sequence. When the homology search was performed, MicroSeq Bacterial Full Gene Library v.0001 (Applied Biosystems, CA, USA) was used as a target database. In particular, BLAST was used for the homology search against the above-listed databases so that the top 10 sequences in homology rate were obtained. Table 5 shows the results of the homology search.

TABLE 5

Result of homology search by
MicroSeq Bacterial Full Gene Library v.0001

| Difference rate (%) | Bacterial species name |
|---|---|
| 0.53 | *Pseudomonas fluorescens* G (bt) |
| 1.54 | *Pseudomonas agarici* |
| 2.07 | *Pseudomonas taetrolens* |
| 2.07 | *Pseudomonas fusivaginea* |
| 2.14 | *Pseudomonas asplenii* |
| 2.27 | *Pseudomonas fluorescens* |
| 2.27 | *Pseudomonas corrugata* |
| 2.34 | *Pseudomonas lundensis* |
| 2.47 | *Pseudomonas fragi* |
| 2.54 | *Pseudomonas veronii* |

Then, in order to obtain more information, a homology search was performed in an international base sequence database (Genbank/DDBJ/EMBL). In particular, BLAST was used for the homology search against the international base sequence database through an online service provided by the NCBI (National Center for Biotechnology Information http://www.ncbi.nlm.nih.gov/) in the United States. Then, the obtained 16S rDNA base sequence was used to perform a homology search for species considered to be closely related to the microorganism (HFKI-0020) of the genus *Pseudomonas*. Table 6 shows the results of the homology search.

TABLE 6

Result of homology search by international base sequence database

| Entry name | Strain name | Accession No | Identity |
|---|---|---|---|
| Uncultured soil bacterium | | AY699603 | 1489/1497 = 99.5% |
| Uncultured bacterium | | AY661989 | 1489/1497 = 99.5% |
| Uncultured soil bacterium | | AY699601 | 1486/1494 = 99.5% |
| Uncultured soil bacterium | | AY699597 | 1486/1494 = 99.5% |
| *Pseudomonas fluorescens* | ATCC 17573 | AF094730 | 1458/1461 = 99.8% |

As a result of the bacterial and physiological property tests, the microorganism (HFKI-0020) of the genus *Pseudomonas* is indicated to be a rod with characteristics of Gram stainability negative, mobility positive, catalase reaction positive, oxidase reaction positive, and fluorochrome production capable, hence it is indicated as a fluorochrome producing *Pseudomonas*. In addition, the 16S rDNA base sequence analysis also indicated a high homology to the 16S rDNA of fluorochrome producing *Pseudomonas* such as *P. fluorescens* biotype G and *P. agarici*. As such, it is considered to be a fluorochrome producing *Pseudomonas*.

Regarding species classification, *P. fluorescens* biotype G is not the corresponding type strain. Since the ATCC 13525 strain, the type of strain of the *P. fluorescens*, was ranked sixth in the homology search by MicroSeq, a high homology rate is not indicated for the *P. fluorescens* type strain. Several different biotypes, including the above-mentioned species biotype G represented by the ATCC 17518 strain, are known to genealogically exist from the analysis based on the 16S rDNA; and all these biotypes are taxonomically handled as *P. fluorescens*. The group of *P. fluorescens* is yet to be taxonomically organized. Therefore, the microorganism (HFKI-0020) of the present invention is plausibly considered a novel microorganism of the genus *Pseudomonas* at present.

The microorganism (HFKI-0020) of the present invention was domestically deposited in the National Institute of Advanced Industrial Science and Technology, International Patent Organism Depositary (Tsukuba Central 6, 1-1-1 Higashi, Tsukuba, Ibaraki, Japan) granted the deposit number of FERM P-20545 on 20 May 2005, later transferred to the international depositary from the domestic depositary, and granted the deposit number of FERM BP-10592 on 29 Mar. 2006.

Example 1

Hereinafter, the details of the present invention will be described with a reference example and a working example. However, the present invention shall not be limited to those examples.

The *Pseudomonas* sp. HFKI-0020 strain was inoculated in a K28 culture medium (peptone 0.5%, yeast extract 0.1%, and artificial seawater 50%) for shaking culture at 10 degrees Celsius for 72 hours. The bacterial bodies were removed by centrifugation so that a culture supernatant was obtained. With 5 mg of 1-palmitoyl-2-oleoylphosphatidylcholine (16:0/18:1(n-9)-PC) or 1-oleoyl-2-palmitoylphosphatidylcholine (18:1(n-9)/16:0-PC) as a substrate, diethyl ether (1 ml) was added to the culture supernatant (1 ml) making a total of 2 ml. After 24 hours of agitation at 10 degrees Celsius, lipids were extracted by the Folch method, and then lysophosphatidylcholine (LPC) was fractionated by silica gel TLC (thin layer chromatography). The constituent fatty acids of the LPC were obtained as methyl ester by the hydrogen chloride-methanol method, and then a quantitative analysis was performed by gas chromatography. Table 7 shows the raw materials and the fatty acid composition of the LPC.

TABLE 7

| Strain | | (%) | | | |
|---|---|---|---|---|---|
| | | 16:0/18:1PC | | 18:1/16:0PC | |
| | | C16:0 | C18:1 | C18:1 | C16:0 |
| HFKI0020 | Raw material PC | 44.1 | 56.9 | 43.2 | 56.8 |
| | LPC | 0 | 100 | 2.5 | 97.5 |

Table 7 shows the fatty acid composition (mol %) of the LPC produced from a hydrolysis reaction of synthesized PC by using a culture supernatant of the *Pseudomonas* sp. HFKI-0020 strain. Although fatty acids were detected at the sn-1 and sn-2 positions from the LPCs in both substrates, the acyl group at the sn-1 position was selectively hydrolyzed, remaining many fatty acids at the sn-2 position. Therefore, it was confirmed that phospholipase $A_1$ activity exists as a major hydrolysis activity among the culture supernatant used as an enzyme solution.

The *Pseudomonas* sp. HFKI-0020 strain was inoculated in a K28 culture medium (peptone 0.5%, yeast extract 0.1%, and artificial seawater 50%) for shaking culture at 10 degrees Celsius for 72 hours. The bacterial bodies were removed by centrifugation so that a culture supernatant was obtained.

With 10 micrograms of soybean oil as a substrate, diethyl ether (0.5 ml) was added to the culture supernatant (0.5 ml), and then agitated for 24 hours at 10 degrees Celsius. As a result of spreading the reacting solution in silica gel TLC, the production of free acids was not detected because the hydrolysis was not observable. Therefore, it was confirmed that this culture supernatant does not demonstrate lipase activity.

INDUSTRIAL APPLICABILITY

The present invention is applicable for industrial mass-emulsification of food and cosmetics by separating and refining enzymes with phospholipase $A_1$ activity in a culture solution.

The invention claimed is:

1. A biologically pure culture of a microorganism of the genus *Pseudomonas* that produces an enzyme with phospholipase $A_1$ activity, wherein the microorganism has the following bacterial properties and the following physiological and biochemical properties;

(A.) Bacterial properties
(1) Cell shape: Width 0.8 to 1.0 micrometer, Length 2.0 to 3.0 micrometers
(2) Gram stainability: Negative
(3) Presence of spores: Negative
(4) Mobility: Positive
(5) Colony shape (Cultivation for 48 hours)
   (a) Diameter: 2.0 to 3.0 mm
   (b) Color tone: Lemon yellow
   (c) Shape: Circular
   (d) Topography: Lens shaped
   (e) Fringe: Whole border
   (f) Surface shape: Smooth
   (g) Transparency: Opaque
   (h) Viscosity: Butter-like
(6) Growth temperature test (degree Celsius)
   (a) At 37 degrees Celsius: Positive
   (b) At 45 degrees Celsius: Weak reaction
(7) Catalase reaction: Positive
(8) Oxidase reaction: Positive
(9) Production of acid and gas from glucose (Acid production/Gas production): Negative/Negative
(10) O/F test (Oxidation/Fermentation): Negative/Negative (B.) Physiological and biochemical properties
(1) Nitrate reduction: Negative
(2) Indole production: Negative
(3) Glucose acidification: Negative
(4) Arginine dihydrolase: Positive
(5) Urease: Negative
(6) Esculin hydrolysis: Negative
(7) Gelatin hydrolysis: Positive
(8) Beta galactosidase: Negative
(9) Glucose assimilation: Positive
(10) L-Arabinose assimilation: Positive
(11) D-Mannose assimilation: Positive
(12) D-Mannitol assimilation: Positive
(13) N-acetyl-D-glucosamine assimilation: Positive
(14) Maltose assimilation: Negative
(15) Potassium gluconate assimilation: Positive
(16) n-Capric acid assimilation: Positive
(17) Adipic acid assimilation: Negative
(18) dl-Malic acid assimilation: Positive
(19) Sodium citrate assimilation: Positive
(20) Phenyl acetate assimilation: Negative
(21) Cytochrome oxidase: Positive
(22) Fluorochrome production on King's B agar medium: Positive.

2. A method of manufacturing 2-acyl lysophospholipids comprising hydrolyzing phospholipids in order to obtain the 2-acyl lysophospholipids by using the enzyme with the phospholipase $A_1$ activity produced by the biologically pure culture of the microorganism as claimed in claim 1.

3. The method of manufacturing 2-acyl lysophospholipids as claimed in claim 2, wherein the enzyme is in a culture solution.

4. A biologically pure culture of *Pseudomonas* HFKI-0020 (FERM AP-20545) that produces an enzyme with phospholipase $A_1$ activity.

5. A method of manufacturing 2-acyl lysophospholipids comprising hydrolyzing phospholipids in order to obtain the 2-acyl lysophospholipids by using the enzyme with the phospholipase $A_1$ activity produced by the biologically pure culture of *Pseudomonas* HFKI-0020 (FERM AP-20545) as claimed in claim 4.

6. The method of manufacturing 2-acyl lysophospholipids as claimed in claim 5, wherein the enzyme is in a culture solution.

7. A biologically pure culture of a microorganism of the genus *Pseudomonas* that produces an enzyme with phospholipase $A_1$ activity, wherein the base sequence of the 16S rRNA gene has more than 99.8% sequence identity with SEQ ID NO:1.

8. A method of manufacturing 2-acyl lysophospholipids comprising hydrolyzing phospholipids in order to obtain the 2-acyl lysophospholipids by using the enzyme with the phospholipase $A_1$ activity produced by the biologically pure culture of the microorganism as claimed in claim 7.

9. The method of manufacturing 2-acyl lysophospholipids as claimed in claim 8, wherein the enzyme is in a culture solution.

10. The biologically pure culture of the microorganism as claimed in claim 7, wherein the base sequence of the 16S rRNA gene is SEQ ID NO:1.

* * * * *